United States Patent [19]
McGregor

[11] 3,980,177
[45] Sept. 14, 1976

[54] CONTROLLED RELEASE SUTURE

[75] Inventor: Walter McGregor, Somerset, N.J.

[73] Assignee: Johnson & Johnson, New Brunswick, N.J.

[22] Filed: Oct. 21, 1974

[21] Appl. No.: 516,549

Related U.S. Application Data

[60] Division of Ser. No. 409,974, Oct. 26, 1973, Pat. No. 3,890,975, which is a continuation-in-part of Ser. No. 258,159, May 31, 1972, abandoned.

[52] U.S. Cl. ............................ 206/63.3; 128/335.5; 128/339
[51] Int. Cl.² .......................................... A61B 17/06
[58] Field of Search ............ 128/335.5, 339; 163/1, 163/5; 223/102; 29/517; 206/63.3

[56] References Cited
UNITED STATES PATENTS

| | | | |
|---|---|---|---|
| 2,014,170 | 9/1935 | Everett | 128/339 |
| 2,411,079 | 11/1946 | Baule | 128/339 |
| 2,620,028 | 12/1952 | Kohut | 128/339 X |
| 3,736,646 | 6/1973 | Schmitt et al. | 128/339 X |
| 3,799,169 | 3/1974 | Beroff et al. | 128/339 |

Primary Examiner—William Price
Assistant Examiner—Joseph M. Moy
Attorney, Agent, or Firm—W. R. Eberhardt

[57] ABSTRACT

A needle-suture combination is provided which has a suture pull-out value between 3 ounces and 26 ounces. The suture, one end of which is sized with a resin and smaller in diameter than the rest of the suture, is manufactured by placing the suture under tension, immersing a small section of the suture in a liquid resin solution, and drying to remove the solvent. The tension is then relaxed and the sized end of the suture inserted into a needle which is swaged to predetermined dimensions.

9 Claims, 14 Drawing Figures

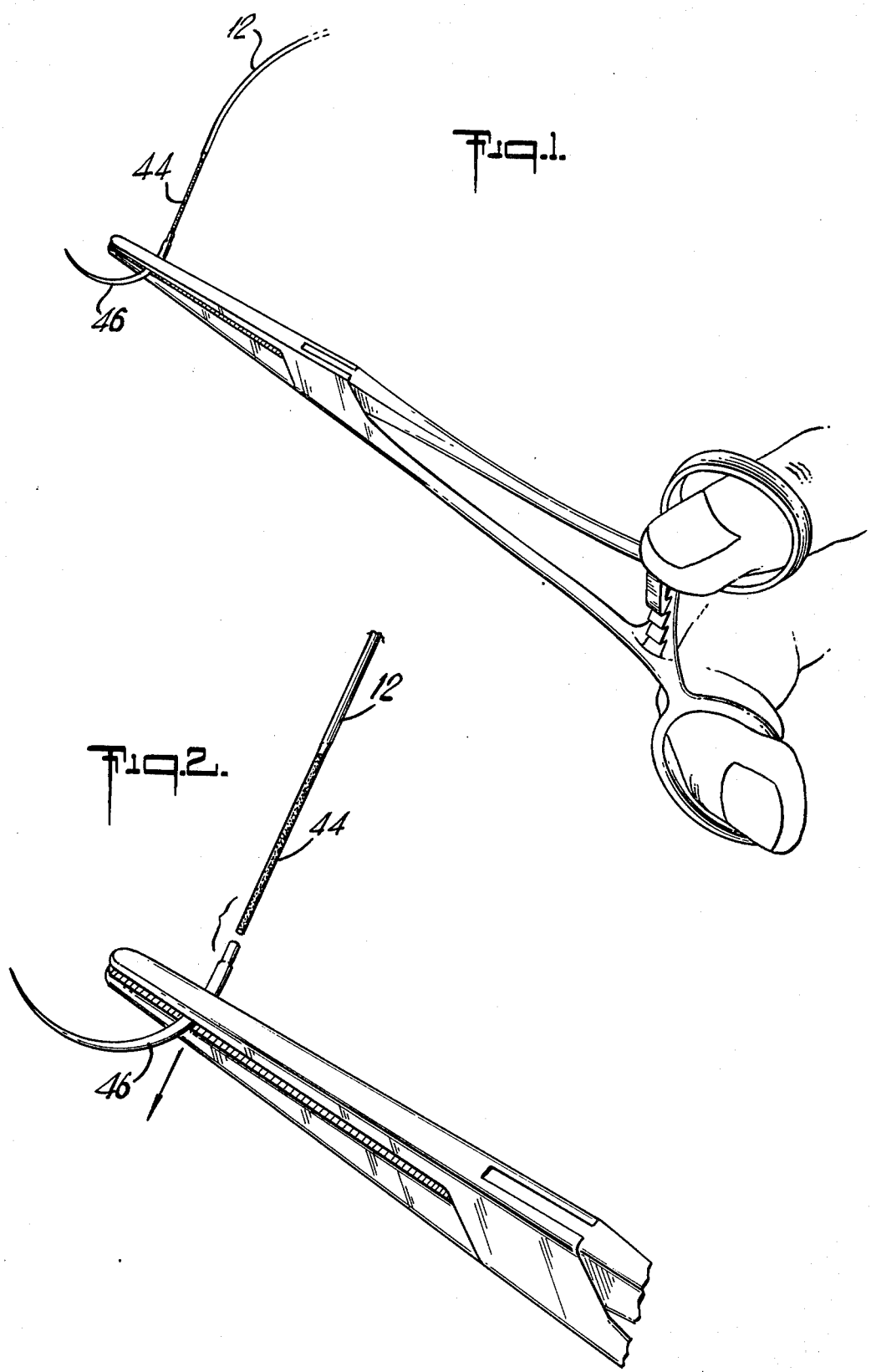

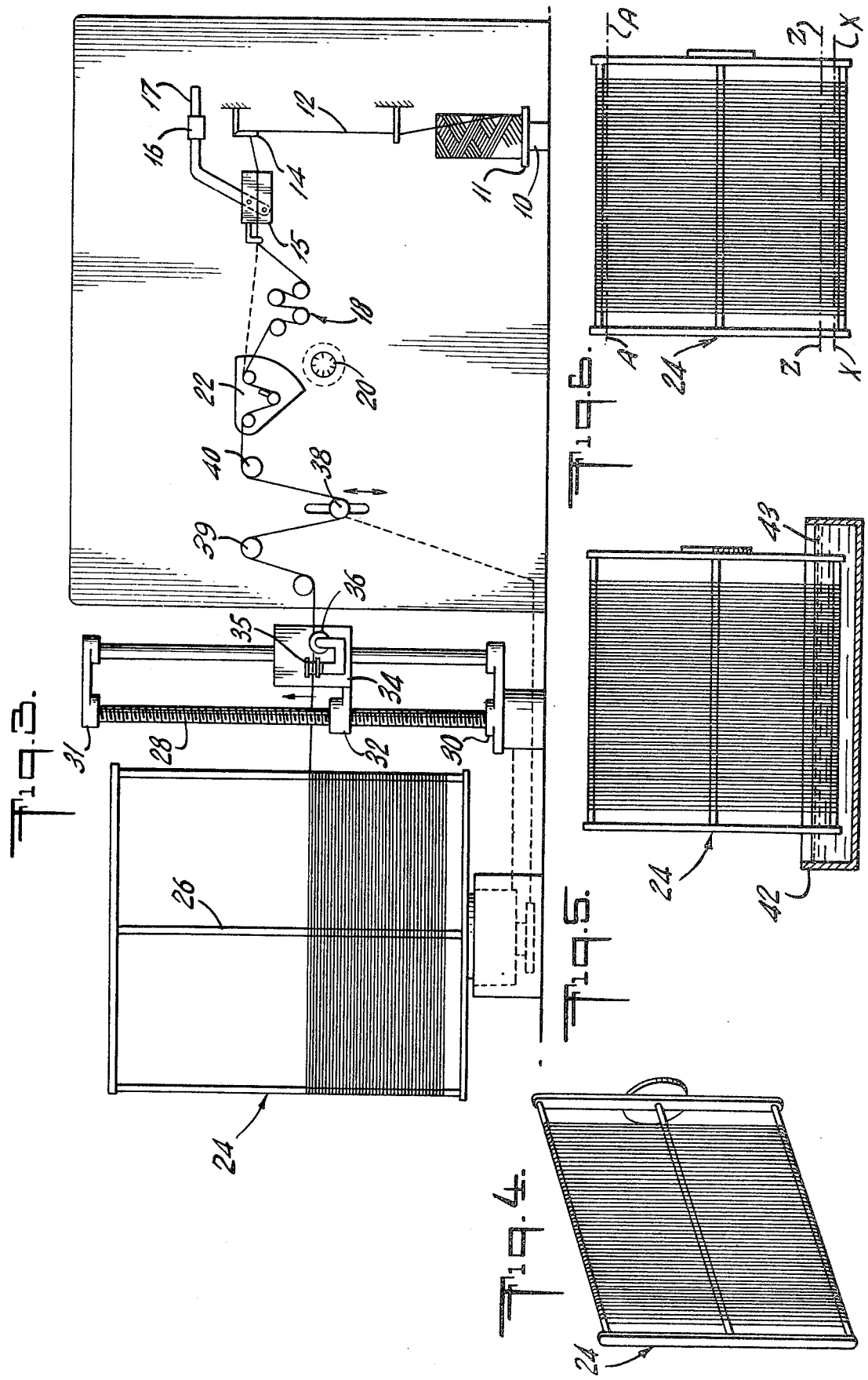

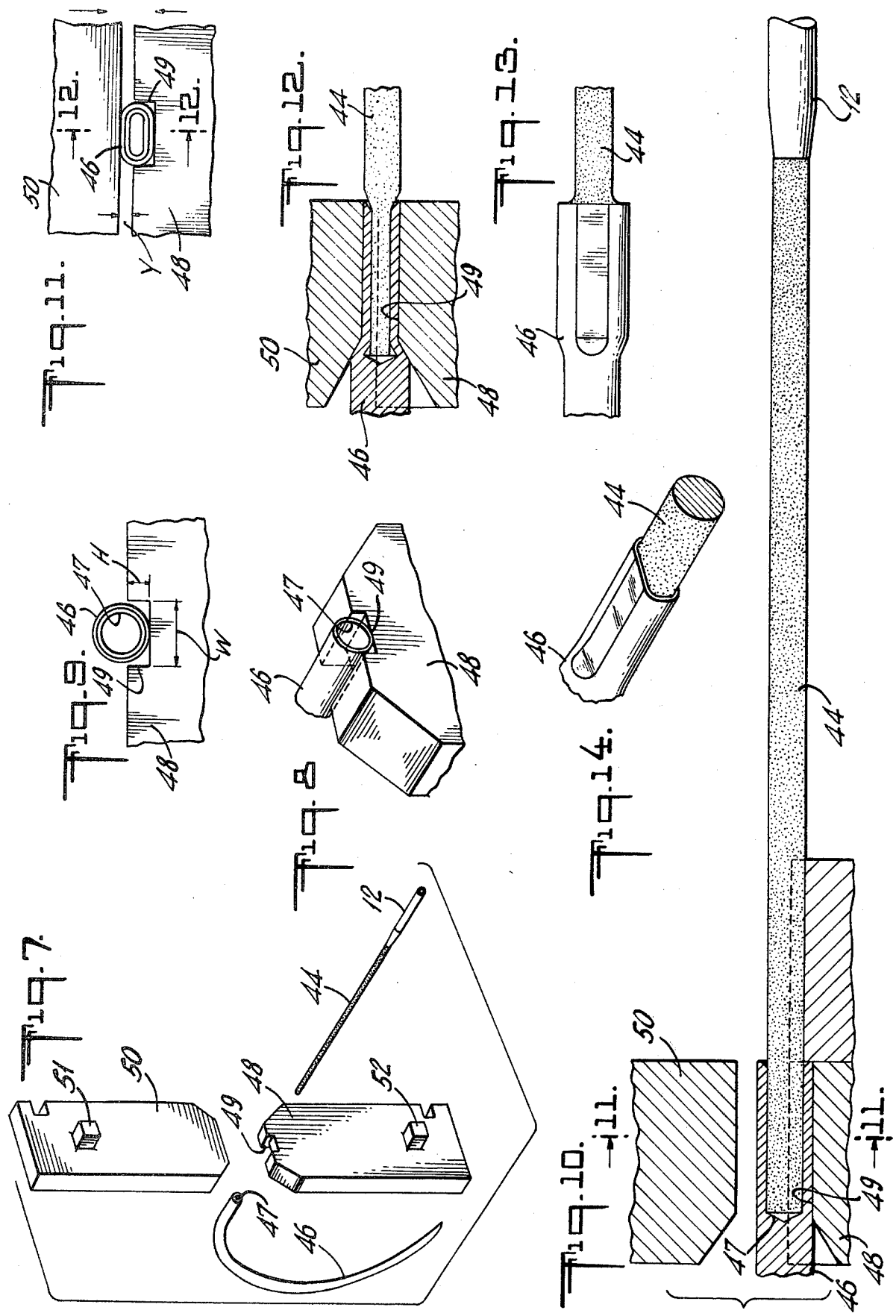

CONTROLLED RELEASE SUTURE

This is a division of Application Ser. No. 409,974 filed Oct. 26, 1973, now U.S. Pat. No. 3,890,975 which in turn is a continuation in part of U.S. Application Ser. No. 258,159 filed May 31, 1972 and now abandoned.

BACKGROUND OF THE INVENTION

In many surgical procedures, surgeons use a technique which employs a non-needled suture and an eyed needle. The needle is threaded by the nurse and the surgeon takes one pass through the tissue using a needleholder. He slips the needle off the suture, returns the needle to the nurse, and is ready for another threaded needle from the nurse. An assistant follows behind and ties the suture.

Surgeons find that this technique is more simple than using a needled item and cutting the suture with a scissors after each pass. However, the time required for threading results in a significant waste of expensive operating room time.

The security of attachment of eyeless needles to absorbable surgical sutures or to nonabsorbable surgical sutures is prescribed in the *U.S. Pharmacopoeia*, Vol. XVIII at Page 944 (also see *U.S. Pharmacopoeia*, Vol. XVII, Page 919). It has been the practice of suture manufacturers in the United States and abroad to securely attach the suture to the needle by swaging or with an adhesive so that the minimum pull-out standard recited in the *U.S. Pharmacopoeia* is met or exceeded. The conversion of the *U.S. Pharmacopoeia* minimum standard on needle attachment from kilograms to ounces is summarized in the following table.

| MINIMUM LIMITS ON NEEDLE ATTACHMENT | | | | |
| --- | --- | --- | --- | --- |
| | AVERAGE | | INDIVIDUAL | |
| SIZE | Kg. | Oz. | Kg. | Oz. |
| 8/0 | 0.068 | 2.39 | 0.036 | 1.26 |
| 7/0 | 0.091 | 3.20 | 0.045 | 1.58 |
| 6/0 | 0.168 | 5.92 | 0.082 | 2.89 |
| 5/0 | 0.226 | 7.97 | 0.113 | 3.98 |
| 4/0 | 0.453 | 15.97 | 0.226 | 7.97 |
| 3/0 | 0.679 | 23.63 | 0.318 | 11.21 |
| 2/0 | 1.1 | 38.8 | 0.453 | 15.96 |
| 1/0 | 1.5 | 52.896 | 0.453 | 15.96 |
| 1 | 1.8 | 63.48 | 0.590 | 20.81 |
| 2 & larger | 1.8 | 63.48 | 0.680 | 23.98 |

It will be noted from the above table that separation of the suture from the needle is relatively easy if the suture is size 5/0 or smaller since the average force required is less than 8 ounces. On the other hand, the minimal average force required to separate a size 4/0 suture (diameter 7.0 mils. to 9.5 mils.) from the needle is at least about 16 ounces and because needles are swaged to make quite certain that the minimum *U.S. Pharmacopoeia* standards are met, many individual samples require forces in excess of 2 pounds to detach the needle from the suture.

There is a need for a needle-suture combination that has the convenience of the needle being preattached to the suture and yet permits separation of the needle from the suture without the necessity of cutting with a scissors.

One approach to this problem is described in copending Application Ser. No. 252,176, filed May 11, 1972 (ETH-363). This approach involves manufacturing the needle with an open channel at the blunt end thereof sized to receive a suture. The suture is bonded to the channel with an adhesive that prevents "pull-out" of the suture as it passes through tissue. After suturing, the surgeon may easily remove the needle from the suture by turning the needle so that the channel is at an angle of about 90° to the direction of the suture and peeling the suture out of the channel.

This approach has one disadvantage in that many surgeons prefer a drilled needle over a channel needle because of the uniform cross-section at the end of the needle and the smooth transition between the needle and the attached suture.

Needle-suture combinations manufactured in accordance with the present invention are characterized by an average suture pull-out value substantially lower than the minimum average force specified in the *U.S. Pharmacopoeia*. Moreover, as will be described hereinafter, changes have been made in the manufacturing processes whereby the variation of the pull-out value from the mean is reduced.

It is an advantage of the product of the present invention, therefore, that the surgeon may readily remove the needle from the suture by exerting a force of 3 to 26 ounces and thereby save the time previously required to cut the suture.

The present invention is directed to needlesuture combinations wherein the suture is of large size, i.e., size 4/0 and larger (diameter greater than 7.0 mils.). The average pull-out value of the needle-suture combinations of the present invention is less than that required by the *U.S. Pharmacopoeia* and the needle may be removed from the suture by a straight pull of 3 to 26 ounces.

In accordance with the present invention, a needle-suture combination characterized by suture "pull-out" value between 3 ounces and 26 ounces and having a substantially uniform cross-section is manufactured by sizing one end of a braided suture with a resin; inserting the sized end of the suture into a drilled needle or preclosed channel needle and swaging the needle to predetermined dimensions. By proper control of the diameter of that end of the suture which is placed in the needle, the diameter of the needle hole and the swaging process, the needle-suture combination produced will have a suture pull-out value between 3 ounces and 26 ounces. It has been noted that if the bond between the needle and its attached suture is sufficient to withstand stand a pull of 3 ounces, the suture will not separate from the needle as a surgeon passes the needle through tissue. Yet, the needle can easily be removed from the suture at any time by simply pulling on the needle with a force of about 26 ounces.

It is an object of the present invention, therefore, to make available to the surgeon a needle-suture combination useful in suturing, and characterized by a needle-suture attachment that will permit facile removal of the needle from the suture without cutting the suture with a scissors.

Another object of this invention is to provide the surgeon with a needle-suture combination that will reduce the time that the surgical patient must spend in the operating room.

Yet another object of the invention is to provide the surgeon with a needle-suture combination that will permit separation of the needle from the suture after suturing by a slight pull upon the needle.

To achieve a controlled pull-out value of a needlesuture combination that is no less than about 3 ounces nor more than about 26 ounces, it is important that the physical dimensions of the needle, the hole in the end of the needle, and the diameter of the suture be uniform. The manufacture of surgical needles to precise dimensions has been done for many years, and it is well within the skill of the art to control the diameter of the needle and the size of the drilled hole to ± 0.0005 inches. The suture that must be attached to the needle, however, presents a more difficult problem. In the case of a synthetic monofilament suture, for example, the diameter may vary with the spinning, drawing, or annealing conditions. Braided sutures and covered sutures present a more difficult problem as the construction of the braid and adjustment of the braider compound any variability that may be present in the yarn. Moreover, the end of a braided or covered suture has a characteristic not found in monofilament sutures in that it will "broom" or open upon cutting. Since it is this cut end of a braided suture that is inserted into the drilled needle hole, it is necessary to hold the diameter of the suture end to within tolerances similar to that for the drilled needle hole to assure a "pull-out" force with a narrowly defined range. In accordance with the present invention, the diameter of a braided suture may be carefully controlled by winding the braided strand on a rack under tension and immersing that section of the suture strand which is to be cut for insertion into the needle in an adhesive or bonding resin while maintaining the strand under tension. The rack is then removed from the resin solution and air dried. The dried adhesive composition which coats and impregnates the braided suture stabilizes the diameter to that achieved under tension. The binding resin or adhesive prevents "brooming" when the suture is cut and the diameter of the suture does not change even after the tension is relaxed.

The suture utilized in the present invention may be absorbable, i.e., catgut, extruded collagen, a braided polyhydroxyacetic ester, a synthetic copolymer of L(-) lactide and glycolide; or nonabsorbable, i.e., braided silk, nylon, polypropylene, cotton, linen, or polyester.

The adhesive that is used to coat the suture while it is retained under tension may be any non-toxic adhesive composition, either organic, inorganic or a hybrid. Suitable organic materials are such natural products as starch, dextrin, asphalt, animal and vegetable proteins, natural rubber, shellac; semi-synthetic products such as cellulose nitrate and the other cellulosics, polyamides derived from dimer acids, castor-oil based polyurethanes; such well-known synthetic resins as vinyl-type addition polymers, both resins and elastomers: polyvinyl acetate, polyvinyl alcohol, acrylics, unsaturated polyesters, butadiene/acrylonitrile, butadiene/styrene, neoprene, butyl rubber, polyisobutylene; and polymers formed by condensation and other step-wise mechanisms, i.e., epoxies, polyurethanes, polysulfide rubbers, and the reaction products of formaldehyde with phenol, resorcinol, urea, and melamine. Particularly preferred as bonding compositions are the epoxide resins and polyester resins.

The invention will become more readily apparent upon consideration of the following detailed description when taken in connection with the accompaying drawings wherein:

FIG. 1 is a perspective view of the needlesuture combination of the present invention. The length of the resin-coated end of the suture has been exaggerated for clarity;

FIG. 2 is an enlarged view illustrating separation of the needle from the suture;

FIG. 3 is a front elevation of apparatus useful in winding sutures under tension;

FIG. 4 is a perspective view of a braided suture strand wound on a reel under tension;

FIG. 5 is a front elevation, partly in section, which illustrates coating the braided suture strand while under tension on the reel with a resin solution;

FIG. 6 illustrates the reel with the tensioned suture strand in place after the sizing step;

FIG. 7 is a perspective view showing elements of an apparatus useful in swaging the needle-suture combination of the present invention;

FIG. 8 is an enlarged fragmentary view of the anvil of the swaging apparatus illustrated in FIG. 7 with a drilled needle in place;

FIG. 9 is a fragmentary end view of the anvil shown in FIG. 8;

FIG. 10 is an enlarged sectional view of the elements illustrated in FIG. 7 as seen from the left, with a needle and suture in position for swaging. The length of the resin-coated end of the suture is exaggerated for clarity;

FIG. 11 is a vertical sectional view along Line 11—11 of FIG. 10 showing the swaging apparatus in its closed position;

FIG. 12 is a vertical sectional view along Line 12—12 of FIG. 11;

FIG. 13 is an enlarged fragmentary plan view of the needle-suture combination, the maximum dimension of the needle being exaggerated to better show the effect of swaging; and FIG. 14 is a fragmentary perspective view of the needle-suture combination of FIG. 13.

The apparatus illustrated in FIG. 3 is designed to wind a strand of suture material, such as braided silk, on to an open rack under tension. It includes in part, a spindle 10 that supports a spool 11 of braided silk 12. The silk strand from the spool passes over a guide 14 and through a mechanical friction brake 15. The tension applied to the moving strand by the brake 15 may be adjusted by sliding a movable weight 16 along its supporting rod 17.

From the mechanical brake 15, small size strands (size 3/0 and smaller) pass directly to the tensiometer as indicated by the dotted line in FIG. 1. Sutures that are larger in diameter than size 3/0 (size 2/0 and larger) pass from the mechanical brake 15 around the rollers of a magnetic brake 18 which may be adjusted to increase or decrease the tension applied to the moving strand by means of a rheostat 20. The tension applied to the moving strand is monitored by a tensiometer 22.

The tensioned strand is taken up on a rack 24 which is rotated about its vertical axis 26 by a motor (not shown). The rack as it rotates, is mechanically linked with a screw 28 mounted for rotation in a lower bearing 30 and upper bearing 31. This screw engages the threads of a nut 32 that is integral with a bracket 34. The pitch of the screw and its angular velocity are such as to move the bracket and associated idler pullies 35 and 36 upwardly in the direction of the arrow, thereby winding the tensioned strand evenly upon the rack.

To complete the description of the tensioning apparatus, a cam-actuated dancer roll 38 moves vertically up and down between idler rollers 39 and 40 as indicated by the arrows. The dancer roll compensates for any change in the tension that would otherwise occur by reason of variation in the linear acceleration of the suture material as the rack rotates at a constant angular velocity.

After the braided strand has been wound evenly on the rack, the end is tied to retain the tension and the rack with the braided strand in place is removed from the tensioning apparatus and an adhesive or binder resin is applied (FIGS. 4, 5, and 6). The rack 24 is immersed to a depth of about 1.5 inches in a container 42 of resin solution 43 for approximately 5 minutes as shown in FIG. 5 to assure penetration of the binding resin into the interstices of the braid. The rack is then removed from the container and air dried at room temperature. The extent of the resin coating thus applied to the braided strand is indicated by the dotted Line Z—Z in FIG. 6.

The resin-coated sutures are then removed from the rack by cutting along the Lines X—X and A—A of FIG. 6. The sutures so obtained have a length slightly less than the width of the rack and are tipped at one end for a distance of about 0.75 inches. As best shown in FIG. 10, the resincoated end 44 of the suture 12 is smaller in diameter than the remainder of the suture.

If it is desired to manufacture a double-armed suture, i.e., a suture having a needle attached to both ends, the width of the rack 24 is adjusted appropriately and the sutures are removed from the rack by making a single cut along the Line X—X.

The swaging of the resin-coated end 44 of a suture into a drilled needle will be described with reference to FIGS. 7 through 14. Swaging is accomplished by placing a needle 46 having a drilled hole 47 at the blunt end thereof on an anvil 48 and striking the drilled end of the needle with a hammer 50 to compress the drilled hole.

In practice, the resin-coated end 44 of the suture is inserted into the drilled hole 47 of the needle as best shown in FIG. 10; the drilled end of the needle is positioned in a depression 49 on the surface of the anvil; and the assembly is swaged by moving the anvil and hammer together in the direction of the arrows as shown in FIG. 11. Stops 51 and 52 on the hammer and anvil respectively limit the motion of the hammer and anvil thereby controlling the clearance Y and the deformation of the needle during the swaging step. The following examples will serve to illustrate the invention.

EXAMPLE I

A size 4/0 black braided silk strand characterized by a diameter (determined optically) of 7.8 mils. is wound on a rack 19¼ inches in width under a tension of 0.6 pounds, using the apparatus illustrated in FIG. 3. One end of the rack is immersed in a container of Xylol as illustrated in FIG. 5 to remove from the braid any wax that may be present. The rack is removed from the container and the Xylol is permitted to evaporate from the braided silk at room temperature.

That end of the rack that has been washed with Xylol is then immersed in a container of a resin solution containing 18 per cent by weight of a linear saturated polyester polymer having a molecular weight in the range of 20,000—30,000 and characterized by a ring and ball softening point of 158°C. (VITEL PE-222 manufactured by Goodyear Chemical Division of the Goodyear Tire & Rubber Company, P.O. Box 2008, New Brunswick, New Jersey 08903). The rack is immersed to a depth of about 1¼ inches for about 5 minutes.

The rack is removed from the resin solution and air dried at room temperature for a minimum of ½ hour. The sutures are then removed from the rack by cutting along the Lines X—X and A—A. The sutures so obtained are approximately 18 inches in length and the resin-coated end measures about 1 inch ± ¼ inch. The diameter of the resin-coated end is 7.5 mils. (determined optically).

A needle-suture combination having a pull-out value between 3 and 26 ounces is manufactured by inserting the resin-coated end of this suture into a needle of the type illustrated in FIG. 7 characterized by an outside diameter of 22 mils. and a drilled hole in the blunt end 10.4 mils. in diameter. The needle is placed in an anvil that has a width W (FIG. 9) of 24 mils. The heighth H (FIG. 9) of the depression in the anvil is 11 mils. The clearance Y is so adjusted that the cross-section of the swaged needle as viewed in FIG. 11 measures 24.3 mils. by 16.3 mils.

During the manufacturing process, every twentyfifth needle-suture combination is pulled and the force required to separate the needle from the suture recorded. The average straight pull-out value for this production run (Batch FA-0744) is 12.34 ounces. The pull-out values vary from a minimum of 4 ounces to a maximum of 26 ounces.

EXAMPLE II

A size 3/0 black braided silk strand characterized by a diameter (determined optically) of 9.9 mils. is wound on a rack 19¼ inches in width under a tension of 0.9 pounds, using the apparatus illustrated in FIG. 3. One end of the rack is immersed in a container of Xylol as illustrated in FIG. 5 to remove from the braid any wax that may be present. The rack is removed from the container and the Xylol is permitted to evaporate from the braided silk at room temperature.

That end of the rack that has been washed with Xylol is then immersed in a container of a resin solution as described in Example I above.

The rack is removed from the resin solution and air dried at room temperature for a minimum of ½ hour. The sutures are then removed from the rack by cutting along the Lines X—X and A—A. The sutures so obtained are approximately 18 inches in length and the resin-coated end measures about 1 inch ± ¼ inch. The diameter of the resin-coated end (determined optically) is 9.5 mils.

A needle-suture combination having a pull-out value between 3 and 26 ounces is manufactured by inserting the resin-coated end of this suture into a needle of the type illustrated in FIG. 7 characterized by an outside diameter of 24 mils. and a drilled hole in the blunt end 13 mils. in diameter. The needle is placed in an anvil that has a width W (FIG. 9) of 27 mils. The heighth H (FIG. 9) of the depression in the anvil is 12 mils. The clearance Y is so adjusted that the cross-section of the swaged needle as viewed in FIG. 11 measures 27 mils. by 17 mils.

During the manufacturing process, every twentyfifth needle-suture combination is pulled and the force required to separate the needle from the suture recorded. The average straight pull-out value for this production run (Batch FA-0428) is 12.42 ounces. The pull-out values vary from a minimum of 4 ounces to a maximum of 26 ounces.

EXAMPLE III

A size 3/0 black braided silk strand was tipped as described in Example II above and swaged to a needle characterized by an outside diameter of 39 mils. and a drilled hole in the blunt end of 13 mils. The needle is placed in an anvil that has a width W (FIG. 9) of 42.5 mils. The heighth H (FIG. 9) of the depression in the anvil is 19 mils. The clearance Y is so adjusted that the crosssection of the swaged needle as viewed in FIG. 11 measures 42.5 mils. by 32 mils.

The needle-suture combinations so obtained are placed in sealed envelopes, eight needle-suture combinations in one envelope. One dozen of these envelopes are packaged in one box. Fifty boxes, or 4,800 needle-suture combinations, are manufactured in one production run. The product is sterilized by Cobalt-60 radiation.

Sixty needle-suture samples randomly selected from this production batch of 4,800 needle-suture combinations (Batch FA-0175) are tested by pulling to separate the needle from the suture and the force required is recorded. The average straight pull-out value for this product run is 10.64 ounces. The pull-out values vary from a minimum of 4 ounces to a maximum of 21 ounces.

EXAMPLE IV

A size 2/0 black braided silk strand characterized by a diameter (determined optically) of 12.9 mils. is wound on a rack 19¼ inches in width under a tension of 1.4 pounds, using the apparatus illustrated in FIG. 1. One end of the rack is immersed in a container of Xylol as illustrated in FIG. 5 to remove from the braid any wax that may be present. The rack is removed from the container and the Xylol is permitted to evaporate from the braided silk at room temperature.

That end of the rack that has been washed with Xylol is then immersed in a container of a resin solution as described in Example I above.

The rack is removed from the resin solution and air dried at room temperature for a minimum of ½ hour. The sutures are then removed from the rack by cutting along the Lines X—X and A—A. The sutures so obtained are approximately 18 inches in length and the resin-coated end measures about 1 inch ± ¼ inch. The diameter of the resin-coated end (determined optically) is 12.6 mils.

A needle-suture combination having a pull-out value between 3 and 26 ounces is manufactured by inserting the resin-coated end of this suture into a needle of the type illustrated in FIG. 7 characterized by an outside diameter of 26 mils. and a drilled hole in the blunt end 16 mils. in diameter. The needle is placed in an anvil that has a width W (FIG. 9) of 28.5 mils. The heighth H (FIG. 9) of the depression in the anvil is 13 mils. The clearance Y is so adjusted that the cross-section of the swaged needle as viewed in FIG. 11 measures 28 mils. by 18 mils.

The needle-suture combinations so obtained are placed in sealed envelopes, eight needle-suture combinations in one envelope. One dozen of these envelopes are packaged in one box. Fifty boxes, or 4,800 needle-suture combinations, are manufactured in one production run. The product is sterilized by Cobalt-60 radiation.

Sixty needle-suture samples randomly selected from this production batch of 4,800 needle-suture combinations (Batch FA-0048) are tested by pulling to separate the needle from the suture and the force required is recorded. The average straight pull-out value for this production run is 13.72 ounces. The pull-out values vary from a minimum of 3 ounces to a maximum of 21.5 ounces.

EXAMPLE V

A size 2/0 black braided silk strand was tipped as described in Example IV above and swaged to a needle characterized by an outside diameter of 39 mils. and a drilled hole in the blunt end of 16 mils. The needle is placed in an anvil that has a width W (FIG. 9) of 42.5 mils. The heighth H (FIG. 9) of the depression in the anvil is 19 mils. The clearance Y is so adjusted that the cross-section of the swaged needle as viewed in FIG. 11 measures 42.5 mils. by 32 mils.

During the manufacturing process, every twenty-fifth needle-suture combination is pulled and the force required to separate the needle from the suture recorded. The average straight pull-out value for this product run (Batch FA-0139) is 11.93 ounces. The pull-out values vary from a minimum of 5 ounces to a maximum of 25 ounces.

EXAMPLE VI

A size 0 black braided silk strand characterized by a diameter (determined optically) of 15.8 mils. is wound on a rack 19¼ inches in width under a tension of 2 pounds, using the apparatus illustrated in FIG. 1. One end of the rack is immersed in a container of Xylol as illustrated in FIG. 5 to remove from the braid any wax that may be present. The rack is removed from the container and the Xylol is permitted to evaporate from the braided silk at room temperature.

That end of the rack that has been washed with Xylol is then immersed in a container of a resin solution as described in Example I above.

The rack is removed from the resin solution and air dried at room temperature for a minimum of ½ hour. The sutures are then removed from the rack by cutting along the Lines X—X and A—A. The sutures so obtained are approximately 18 inches in length and the resin-coated end measures about 1 inch ± ¼ inch. The diameter of the resin-coated end (determined optically) is 15.6 mils.

A needle-suture combination having a pull-out value between 3 and 26 ounces is manufactured by inserting the resin-coated end of this suture into a needle of the type illustrated in FIG. 7 characterized by an outside diameter of 39 mils. and a drilled hole in the blunt end 18.7 mils. in diameter. The needle is placed in an anvil that has a width W (FIG. 9) of 41 mils. The heighth H (FIG. 9) of the depression in the anvil is 19 mils. The clearance Y is so adjusted that the cross-section of the swaged needle as viewed in FIG. 11 measures 41 mils. by 32 mils.

The needle-suture combinations so obtained are placed in sealed envelopes, eight needle-suture combinations in one envelope. One dozen of these envelopes are packaged in one box. Fifty boxes, or 4,800 needle-suture combinations, are manufactured in one production run. The product is sterilized by Cobalt-60 radiation.

Sixty needle-suture samples randomly selected from this production batch of 4,800 needle-suture combinations (Batch FA-0266) are tested by pulling to separate the needle from the suture and the force required is recorded. The average straight pull-out value for this product run is 13.1 ounces. The pull-out values vary from a minimum of 5 ounces to a maximum of 24 ounces.

EXAMPLE VII

A needle-suture combination having a pull-out value between 3 and 26 ounces is manufactured by inserting a nylon monofilament strand characterized by a diameter (determined optically) of 9.8 mils. into a needle of the type illustrated in FIG. 7 characterized by an outside diameter of 39 mils. and a drilled hole in the blunt end 13 mils. in diameter. The needle is placed in an anvil that has a width W (FIG. 9) of 42 mils. The heighth H (FIG. 9) of the depression in the anvil is 19 mils. The clearance Y is so adjusted that the cross-section of the swaged needle as viewed in FIG. 11 measures 42 mils. by 32.5 mils.

The average straight pull-out value for a run of 50 samples is 12.5 ounces. The pull-out values vary from a minimum of 5 ounces to a maximum of 17.5 ounces.

The average straight pull-out value for a second run of 50 samples is 12.9 ounces. The pull-out value of this second run varied from a minimum of 6.5 ounces to a maximum of 17.5 ounces.

EXAMPLE VIII

A needle-suture combination having a pull-out value between 3 and 26 ounces is manufactured by inserting a size 3/0 polypropylene monofilament strand having a diameter (determined optically) of 9.7 mils. into a needle of the type illustrated in FIG. 7. The needle has an outside diameter of 39 mils. and a drilled hole in the blunt end 13 mils. in diameter. The needle is placed in an anvil that has a width W (FIG. 9) of 42 mils. The heighth H (FIG. 9) of the depression in the anvil is 19 mils. The clearance Y is so adjusted that the cross-section of the swaged needle as viewed in FIG. 11 measures 42 mils. by 32.4 mils.

The average straight pull-out value for a run of 53 samples is 11.2 ounces. The pull-out values vary from a minimum of 4.5 ounces to a maximum of 18.5 ounces.

Depending upon the stage of manufacture (before or after sterilization) needle-suture combinations made in accordance with the foregoing examples may have an average straight pull-out value as low as 9.35 ounces and as high as 14.7 ounces. Such products are acceptable to the surgeon as a controlled release suture.

The needle-suture combinations of the present invention may be used by the surgeon employing conventional suturing technique as illustrated in FIG. 1. After the suture has been placed, the needle may be separated by a wrist motion snapping the needle off the end of the suture as best illustrated in FIG. 2. The force required to pull the needle from the end of the suture is in the range of from about 3 ounces to about 26 ounces.

The extent to which a suture is compressed during swaging may be calculated from the information given in the patent examples.

Referring now to FIGS. 8, 11, and 13, it will be apparent that thickness of the wall enclosing the needle hole is obtained by subtracting the diameter of the drill hole 47 from the wire diameter 46. The swaged thickness is the minimum diameter after swaging. In Example I, the swaged dimensions as viewed in FIG. 11 measure 24.3 mils. by 16.3 mils. (swaged thickness 16.3 mils.). The minimum clearance is the minimum dimension of the opening that remains within the needle hole following swaging and is obtained by subtracting the wall thickness from the swaged thickness. The compression, i.e., the percent compression of the suture from its original diameter is obtained by dividing the minimum clearance by the original suture diameter. These factors which determine the percent compression of the suture within the needle hole upon swaging are summarized in the following table:

| EXAMPLE | I | II | III | IV | V | VI | VII | VIII |
|---|---|---|---|---|---|---|---|---|
| Wire Diameter | 22 | 24 | 39 | 26 | 39 | 39 | 39 | 39 |
| Drill Hole | 10.4 | 13 | 13 | 16 | 16 | 18.7 | 13 | 13 |
| Wall Thickness | 11.6 | 11 | 26 | 10 | 23 | 20.3 | 26 | 26 |
| Swaged Thickness | 16.3 | 17 | 32 | 18 | 32 | 32 | 32.5 | 32.4 |
| Minimum Clearance | 4.7 | 6 | 6 | 8 | 9 | 11.7 | 6.5 | 6.4 |
| Suture Diameter | 7.5 | 9.5 | 9.5 | 12.6 | 12.6 | 15.6 | 9.8 | 9.7 |
| Percent Compression | 62 | 63 | 63 | 63 | 71 | 75 | 66 | 66 |

The patent examples, therefore, demonstrate that compression of the resin-coated end of the suture within the drilled needle hole to from about 62 per cent to about 75 per cent of its original diameter results in a pull-out value of from about 3 to 26 ounces.

In the appended claims, the term "compressed to from about 62 per cent to about 75 per cent of its original diameter" shall mean that the minimum clearance divided by the original diameter of the resin-coated end of the suture is within the range of about 0.62 to 0.75.

As many apparently widely different embodiments of this invention may be made without departing from the spirit and scope thereof, it is to be understood that the invention is not limited to the specific embodiments thereof except as defined in the following claims.

What is claimed is:

1. A plurality of sterile needle-suture combinations in a package, each of said needle-suture combinations within said package comprising a needle having a recess at the blunt end and a suture having a diameter greater than 7 mils., one end of which is received within said recess and swaged whereby said end is compressed, said needle-suture combinations being characterized by having individual straight pull-out values of from about 3 ounces to about 26 ounces and an average straight pull-out value between about 9 ounces and about 15 ounces.

2. Needle-suture combinations of claim 1 wherein each of the sutures within said package is a multifilament suture, one end of which is coated with a resin and of smaller diameter than the rest of the suture which extends from the needle, said resin-coated end being received within said recess and swaged whereby the resin-coated end is compressed.

3. Needle-suture combinations of claim 2, wherein each of the needles within said package is selected from the group consisting of a curved needle, a straight needle, a cutting edge needle, and a taper point needle.

4. Needle-suture combinations of claim 1, wherein each of the sutures within said package is a covered silk suture.

5. Needle-suture combinations of claim 1, wherein each of the sutures within said package is a braid of a material selected from the group consisting of silk, polyester and nylon.

6. Needle-suture combinations of claim 5, wherein each of the sutures within said package is a polyester selected from the group consisting of polyhydroxyacetic ester and a copolymer of glycolide and L(-)lactide.

7. Needle-suture combinations of claim 5, wherein one end of each of the sutures within said package is coated with a resin selected from the group consisting of epoxy resin and polyester resin.

8. Needle-suture combinations of claim 1, wherein each of the sutures within the package is a monofilament suture.

9. Needle-suture combinations of claim 8, wherein each of the sutures within the package is a material selected from the group consisting of nylon, polypropylene, and polyester.

* * * * *

UNITED STATES PATENT OFFICE
CERTIFICATE OF CORRECTION

Patent No. 3,980,177     Dated September 14, 1976

Inventor(s) Walter McGregor     Page 1 of 2

It is certified that error appears in the above-identified patent and that said Letters Patent are hereby corrected as shown below:

Under Assignee, "Johnson & Johnson, New Brunswick, N.J." should read --- Ethicon, Inc., Somerville, N.J. ---.

In Column 2, line 67, "needlesuture" should read --- needle-suture ---.

In Column 3, line 65, "needlesuture" should read --- needle-suture ---.

In Column 3, line 23, "narrowlydefined" should read --- narrowly-defined ---.

In Column 3, line 63, "accompaying" should read --- accompanying ---.

In Column 6, line 21, "twentyfifth" should read --- twenty-fifth ---.

In Column 6, line 16, "heighth" should read --- height ---.
In Column 6, line 57, "heighth" should read --- height ---.
In Column 7, line 8, "heighth" should read --- height ---.
In Column 7, line 55, "heighth" should read --- height ---.
In Column 8, line 14, "heighth" should read --- height ---.
In Column 8, line 53, "heighth" should read --- height ---.
In Column 9, line 15, "heighth" should read --- height ---.
In Column 9, line 47, "heighth" should read --- height ---.

UNITED STATES PATENT OFFICE
CERTIFICATE OF CORRECTION

Patent No. 3,980,177   Dated September 14, 1976

Inventor(s) Walter McGregor   Page 2 of 2

It is certified that error appears in the above-identified patent and that said Letters Patent are hereby corrected as shown below:

In Column 10, line 36, "about 3 to 26 ounces" should read -- about 3 to about 26 ounces --.

Signed and Sealed this

Tenth Day of May 1977

[SEAL]

Attest:

RUTH C. MASON
Attesting Officer

C. MARSHALL DANN
Commissioner of Patents and Trademarks